United States Patent [19]

Huang

[11] Patent Number: 4,677,210

[45] Date of Patent: Jun. 30, 1987

[54] 1-ARYLALKOXY- AND 1-ARYLALKYLTHIOARYL-2-PYRAZOLINES AS ANTI-INFLAMMATORY OR ANTI-ALLERGIC AGENTS

[75] Inventor: Fu-chih Huang, Leonia, N.J.

[73] Assignee: Rorer Pharmaceutical Corporation, Fort Washington, Pa.

[21] Appl. No.: 746,436

[22] Filed: Jun. 19, 1985

[51] Int. Cl.$^4$ .................. A61K 31/415; A61K 31/47; C07D 231/06; C07D 409/14

[52] U.S. Cl. .................... 514/312; 514/313; 514/314; 514/333; 514/337; 514/341; 514/403; 514/404; 546/153; 546/155; 546/156; 546/157; 546/162; 546/167; 546/170; 546/174; 546/176; 546/177; 546/256; 546/274; 546/279; 548/362; 548/379

[58] Field of Search ............... 546/155, 156, 157, 153, 546/162, 167, 168, 170, 171, 174, 177, 176, 256, 274, 279; 548/362, 379; 514/312, 313, 314, 333, 337, 341, 403, 404, 467

[56] References Cited

U.S. PATENT DOCUMENTS 4,370,339  1/1983  Haviv et al. ............... 514/404
4,432,991  2/1984  Dusza et al. ............... 548/362
4,564,684  1/1986  Copp et al. ............... 548/362

FOREIGN PATENT DOCUMENTS 119449  9/1984  European Pat. Off. ........... 548/379

Primary Examiner—John M. Ford
Assistant Examiner—Kurt G. Briscoe

[57] ABSTRACT

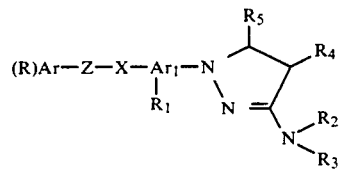

wherein
- Ar and $Ar_1$ are each independently phenyl or naphthyl or a nitrogen, oxygen or sulfur-heterocyclic ring;
- Z is a chemical bond or an alkylene chain containing up to 5 carbons in the principal chain and up to a total of 7 carbons;
- X is O or S;
- R and $R_1$ are independently hydrogen, hydroxy, lower alkoxy, lower alkanoyloxy, halo, cyano, carboloweralkoxy, carboxyloweralkyl, aryloxy or benzyloxy;
- $R_2$, $R_3$, $R_4$ and $R_5$ are independently hydrogen, lower alkyl, lower aralkyl, lower alkenyl, lower alkynyl, aryl or carboxyloweralkyl;

and pharmaceutically acceptable salts thereof have pharmaceutical activity, particularly as lipoxygenase inhibitors possessing anti-inflammatory and anti-allergic properties.

28 Claims, No Drawings

1-ARYLALKOXY- AND 1-ARYLALKYLTHIOARYL-2-PYRAZOLINES AS ANTI-INFLAMMATORY OR ANTI-ALLERGIC AGENTS

FIELD OF THE INVENTION

This invention relates to new chemical compounds possessing valuable pharmaceutical activity, particularly as lipoxygenase inhibitors possessing anti-inflammatory and anti-allergic properties.

DESCRIPTION OF THE PRIOR ART

U.K. patent application GB No. 2 093 832A describes pyrazolines and salts thereof which are anti-inflammatory or anti-allergic agents and have the formula:

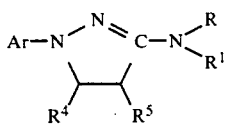

wherein,

Ar is a monocyclic or bicyclic aromatic radical having from 5 to 10 ring atoms selected from carbon and nitrogen, which aromatic radical is optionally substituted in any position of the ring by one or more substituent(s): R is selected from hydrogen, alkyl (optionally substituted by a substituent selected from phenyl which may itself be substituted in any position of the ring by a suitable substituent, and cycloalkyl of from 3 to 6 carbon atoms), alkenyl and alkynyl;

$R^1$ is selected from alkyl (optionally substituted by a substituent selected from phenyl which may itself be substituted in any position of the ring by a suitable substituent, and cycloalkyl of from 3 to 6 carbon atoms), alkenyl and alkynyl; and $R^4$ and $R^5$ are the same or different and are each selected from hydrogen and alkyl.

U.S. Pat. No. 4,447,442 describes 3-substituted amino 1-phenyl-2-pyrazolines and salts thereof of the formula:

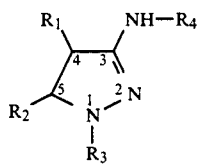

wherein $R_1$ is hydrogen or lower alkyl ($C_1-C_4$); $R_2$ is hydrogen, lower alkyl ($C_1-C_4$), phenyl or

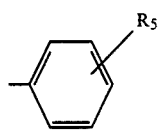

where $R_5$ is halogen; $R_3$ is

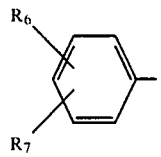

where $R_6$ and $R_7$ are the same or different and may be hydrogen, chloro, fluoro, lower alkyl ($C_1-C_4$), trifluoromethyl or $COCF_3$; $R_4$ is $—CHO$ or $—COCF_3$ with the proviso that when $R_4$ is $—CHO$ then $R_2$ is phenyl or

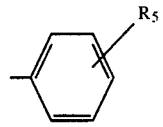

where $R_5$ is halogen. These compounds are disclosed as analgesic, anti-bacterial or anti-fungal agents which are useful for ameliorating the inflammation and/or the progressive joint deterioration characteristic of arthritic disease and preventing the onset of asthmatic symptoms and allergic diseases. Closely related is U.S. Pat. No. 4,451,479 which describes the 3-amino-1-halogenated phenyl-2-pyrazoline and salts thereof of the formula:

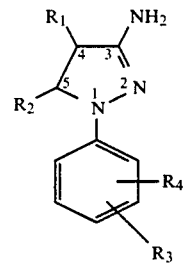

wherein $R_1$ is hydrogen or lower alkyl ($C_1-C_4$), , $R_2$ is phenyl or

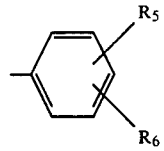

where $R_5$ and $R_6$ are the same or different and are hydrogen, halogen or lower alkyl ($C_1-C_4$), with the proviso that $R_5$ and $R_6$ cannot both be hydrogen; $R_3$ and $R_4$ are the same or different and are hydrogen or halogen with the proviso that $R_3$ and $R_4$ cannot both be hydrogen.

SUMMARY OF THE INVENTION

The present invention provides new anti-inflammatory, anti-hypersensitive and anti-allergic agents represented by the formula:

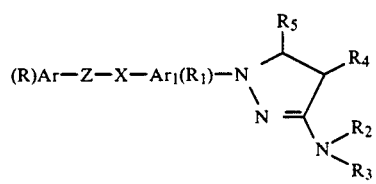

wherein

Ar₁ and Ar₂ are each independently a phenyl or naphthyl or a nitrogen, oxygen or sulfur-heterocyclic ring;

Z is a chemical bond or an alkylene chain containing up to 5 carbons in the principal chain and up to a total of 7 carbons;

X is O or S;

R and $R_1$ are each independently hydrogen, hydroxy, lower alkoxy, lower alkyl, lower alkanoyloxy, halo, cyano carboxy lower alkyl, carboloweralkoxy, carboxy, aryloxy or benzyloxy;

$R_2$, $R_3$, $R_4$ and $R_5$ are independently hydrogen, lower alkyl, lower aralkyl, lower alkenyl, lower alkynyl, aryl or carboxy lower alkyl and pharmaceutically acceptable salts thereof.

DETAILED DESCRIPTION OF THE INVENTION

The heterocyclic rings exemplary of Ar are 5–10 membered rings containing at least one oxygen, sulfur or nitrogen and include the so-called benzoheterocyclic rings. Exemplary heterocyclics include furan, thiophene, pyrrole, pyridine, thiazole, piperazine, oxazole, benzofuran, quinoline, isoquinoline, indole, benzothiophene, benzoxazole and similar heterocyclic rings as well as the N-oxides of the nitrogen-heterocyclics. The preferred heterocyclic groups are quinoline, pyridine and benzothiophene.

Additional variations in the structural formula representing the instant compounds can be effected without significantly altering the therapeutic properties, e.g., lipoxygenase inhibition. For example, the aryl groups can be substituted by one or more of a variety of substituents such as alkyl, aryl, halogen, hydroxy, alkoxy, aryloxy, such as phenoxy, benzyloxy, carboxy, carbalkoxy, carbamoyl, nitrilo, amino, alkylamino, dialkylamino, formyl, trihalomethyl and nitro groups.

The alkyl groups, either alone or within the various substituents defined hereinabove, are preferably lower alkyl, which may be straight or branched-chain and include methyl, ethyl, propyl, isopropyl, butyl, isobutyl, amyl, hexyl, and the like.

Exemplary alkanoyl groups include acetyl, propionyl, butyryl, valeryl, isobutyryl and pivaloyl.

The halo atoms in halo and trihalomethyl are Cl, Br, I and F.

In accordance with the present invention, the preferred compounds are those in which Ar and Ar₁ are phenyl, quinolinyl, pyridyl or benzothiophenyl, Z is methylene, X is oxygen, $R_1$, $R_4$ and $R_5$ are hydrogen, and $R_2$ and $R_3$ are independently H or lower alkyl of up to five carbon atoms in the principal chain.

The compounds of the present invention may contain one or more asymmetric carbon atoms and may exist in racemic and optically active forms. All of these compounds are contemplated to be within the scope of the present invention.

The present compounds can be prepared by art recognized procedures from known compounds or readily preparable intermediates. An exemplary general procedure as described by Duffin, G.F. and Dendall, T.D. in *J. Chem. Soc.*, 1954, 408–415, is as follows:

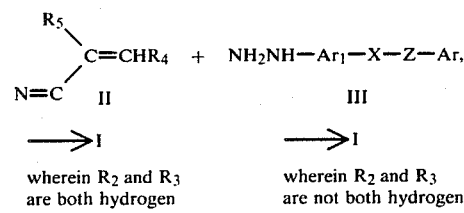

wherein $R_2$ and $R_3$ are both hydrogen wherein $R_2$ and $R_3$ are not both hydrogen The substituents in this scheme are as previously defined.

In accordance with the above reaction scheme, an arylhydrazine (III) is reacted with an α,β-unsaturated nitrile (II) in the presence of a base to afford compounds of Formula I wherein $R_2$ and $R_3$ are both hydrogen. Exemplary α,β-unsaturated nitriles are acrylonitrile, methacrylonitrile, crotonitrile, cinnamonitrile, p-chlorocinnamonitrile, 4-methylcinnamonitrile, butyl acrylonitrile, and the like. Typical bases include sodium ethoxide, potassium methoxide, choline hydrate, sodium hydride, or the like. The reaction is carried out in a solvent that will dissolve both reactants and is inert to both reactants and products as well. Solvents include diethyl ether, tetrahydrofuran, ethanol, propanol, dioxane, methanol, methylene chloride, chloroform, and the like. The aforesaid reactions can be effected at or near reflux temperatures, although temperatures from 0° C. up to the reflux temperature of the reaction mixture can be employed.

The 3-aminopyrazolines can be converted to other derivatives using known reagents and art-recognized procedures. For example, the amino group can be alkylated using alkylating reagents, such as alkyl iodides. In addition, the 3-aminopyrazolines can be treated with acylating agents known in the art, such as the acyl halides, anhydrides, and the like. The amide forming reactions will occur at room temperature or elevated temperatures. The use of elevated temperatures is for convenience in that it permits somewhat shortened reaction periods. The acyl groups can then be transformed to the corresponding alkyl groups by various known methods in the art, such as Wolff-Kishner reduction or Clemmenson reduction. The acylation may be performed in the absence of solvents since liquid reactants such as acetic anhydride can serve as solvents as well. However, it is preferable that solvents be employed in both the acylation and the subsequent reduction reactions. The reactions are carried out in solvents that are inert to the reactants and products and which dissolve the reactants as well. Typical solvents include ether, tetrahydrofuran, dioxane, methylene chloride, ethylene chloride, and the like.

Alternatively, compounds of Formula I may be prepared by cyclization and elimination of water from a compound of Formula IV and optionally converting it to any other desired compound of Formula I,

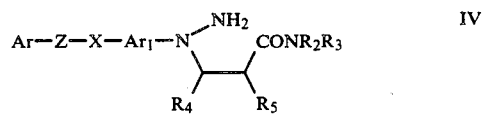

wherein the substituents are as defined in Formula I. The conversion of compounds of Formula IV to compounds of Formula I requires dehydrating agents such as phosphorous oxychloride, dicyclohexylcarbodiimide, and the like. The compound of Formula IV may be prepared by the reaction of the phenylhydrazine (III) with an α,β-unsaturated amide (V):

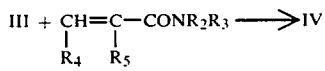

$$III + CH=C-CONR_2R_3 \longrightarrow IV$$
$$\phantom{III + }|\phantom{CH=}|$$
$$\phantom{III + }R_4\phantom{H=}R_5$$

A preferred reaction is where either $R_2$ is other than hydrogen or when $R_2$ is hydrogen, $R_2$ is sterically hindered by $R_3$, which is therefore a group such as tert-butyl, tert-amyl, and the like.

A further method for the formation of compounds of Formula I, wherein $R_2$ is hydrogen and $R_3$ includes a methylene adjacent to the nitrogen atom and preferably does not include alkenyl nor alkynyl, comprises reduction of a compound of Formula VI

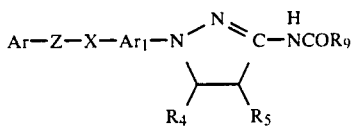

wherein Ar, Z, X, $R_4$ and $R_5$ are as defined hereinabove, and $R_3$ is $CH_2R_9$. Suitable reducing agents are known to those skilled in the art and include diborane, lithium aluminum hydride, and the like.

In all of the reactions described hereinabove, the reactions are carried out in a solvent that will dissolve both reactants and is inert to both reactants and products as well. Solvents include diethyl ether, tetrahydrofuran, methylene chloride, chloroform, dioxane, and the like. The aforesaid reactions can be effected at or near room temperature, although temperatures from 0° C. up to the reflux temperature of the reaction mixture can be employed.

Various substituents on the present new compounds, e.g., as defined in R and $R_1$, can be present in the starting compounds, added to any one of the intermediates or added after formation of the final products by the known methods of substitution or conversion reactions. If the substituents themselves are reactive, then the substituents can themselves be protected according to the techniques known in the art. A variety of protecting groups known in the art may be employed. Examples of many of these possible groups may be found in "Protective Groups in Organic Synthesis" by T.W. Green, John Wiley and Sons, 1981. For example, the nitro groups can be added to the aryl groups by nitration and the nitro group converted to other groups such as amino by reduction and halo by diazotization of the amino group and replacement of the diazo group. Alkanoyl groups can be substituted onto the aryl groups by Friedel-Crafts acylation. The acyl groups can then be transformed to the corresponding alkyl groups by various methods, including the Wolff-Kishner reduction and Clemmenson reduction. Amino groups can be alkylated to form mono and dialkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or conversion reactions can be employed to provide a variety of substituents throughout the molecule of the starting material, intermediates or the final product.

The compounds of the present invention can be administered to the host in a variety of forms adapted to the chosen route of administration, i.e., orally, intravenously, intramuscularly or subcutaneous, topically or inhalation routes.

The active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules, and the like may also contain the following: A binder such as gum tragacanth, acacia, corn starch or gelatin; excipients such as dicalcium phosphate; a disintegrating agent such as corn starch, potato starch, alginic acid, and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amounts in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solutions thereof.

The following Examples further illustrate the invention.

EXAMPLE 1

3-Amino-1-(3-benzyloxyphenyl)-2-pyrazoline

To an ethanolic sodium ethoxide solution (prepared from 0.29 g of sodium and 20 mL of ethanol) was added 2 g of 3-benzyloxyphenylhydrazine hydrochloride and 0.51 g of acrylonitrile. The reaction mixture was refluxed for 5 h and then cooled to room temperature. Solvent was removed in vacuo, residue washed well with water and ether to give 0.4 g of solid. Recrystallization from $CH_2Cl_2$-Hexane gave 0.3 g of pure product: mp 135°–136° C.

EXAMPLE 2

3-Amino-1-(4-benzyloxyphenyl)-2-pyrazoline

Using the procedure of Example 1, and substituting 4-benzyloxyphenylhydrazine hydrochloride for 3-benzyloxyphenylhydrazine hydrochloride, the above product was prepared: mp 148°–149° C.

EXAMPLE 3

3-Ethylamino-1-(4-benzyloxyphenyl)-2-pyrazoline

A. 3-Acetamido-1-(4-benzoyloxyphenyl)-2-pyrazoline

A solution of the product from Example 2 (1.5 g) in 15 mL of acetic anhydride was heated at 60° C for 2 h. The precipitated product was collected on a filter. The crude product 0.7 g was used without further purification.

B. 3-Ethylamino-1-(4-benzyloxyphenyl)-2-pyrazoline

The crude product from A (0.7 g) was added to a suspension of 0.6 g of $LiAlH_4$ in 30 mL of ether and the reaction mixture was refluxed overnight. Excess hydride was decomposed by water dropwise. The organic layer was washed with water, dried and concentrated to give 0.3 g of crude product. The crude compound was converted to its hydrochloride salt in ether by a stream of HCl gas.

In a similar fashion according to the procedures of the preceding examples, the following compounds can be prepared from appropriate starting materials:

3-Amino-1-(3-(2-quinolinylmethoxy)phenyl)-2-pyrazoline
3-Benzylamino-1-(3-benzyloxyphenyl)-2-pyrazoline
3-(Butylamino)-1-(3-benzyloxyphenyl)-2-pyrazoline
3-(4-Carboxybutylamino)-1-(3-phenylethoxyphenyl)-2-pyrazoline
3-Amino-1-(5-benzyloxy-2-pyridyl)-2-pyrazoline
3-Amino-1-(7-benzyloxy-2-quinolinyl)-2-pyrazoline
3-Amino-1-(2-benzothioenylethoxyphenyl)-2-pyrazoline
3-Propylamino-1-(4-benzyloxyphenyl)-2-pyrazoline
3-Pentylamino-1-(3-benzyloxyphenyl)-2-pyrazoline The compounds of the present invention have potent activity in regulating lipoxygenase and, as such, possess therapeutic value in the treatment of inflammatory conditions and allergic responses such as anaphylaxis and asthma.

Lipoxygenases in mammals have been found in the lung, platelets and white cells. They are enzymes capable of oxidizing arachidonic acid into hydroperoxyeicosatetraenoic acids (HPETEs) and their stable products hydroxyeicosatetraenoic acids (HETEs). Lipoxygenases are classified according to the position in the arachidonic acid which is oxygenated. Platelets metabolize arachidonic acid to 12-HETE, while polymorphonuclear (PMN) leukocytes contain 5 and 15 lipoxygenases. It is known that 12-HETE and 5,12-diHETE are chemotactic for human neutrophils and eosinophils, and may augment the inflammation process. 5-HETE is known to be a precursor of slow reacting substance anaphylaxis (SRS-A). The SRS family of molecules, such as leukotrienes B, C and D, have been shown to be potent bronchoconstrictors (see, NATURE, 288, 484–486 (1980). The following protocols describe assays that detect inhibitors of the lipoxygenase. Such inhibitors are believed to be capable of modulating the biosynthesis of the leukotrienes, a property believed to be useful in treating asthma and inflammatory disease states.

Biosynthesis of 12-HETE by Intact Platelets (12-LOX)

Four to five Sprague-Dawley rats (200-300 g) are individually anesthetized with diethylether in a large glass desiccator placed in a hood. A 100 ml beaker packed with cotton which is saturated with ether is placed over the rat's head to prevent the animal from regaining consciousness during the isolation procedure. A twenty ml syringe containing 1.0 ml of 3.8% sodium citrate is used to draw 9 mls of blood from the abdominal aorta. The blood/citrate is then gently mixed and transferred to a 15 ml polypropylene centrifuge tube which is capped and kept at RT.

Platelet Rich Plasma (PRP) is prepared by centrifugation (in a Damon table top centrifuge) of the citrated blood at 200 g for 10 min at room temperature. Platelets are collected by centrifugation of the PRP at 1000 g for 10 min at RT. Platelet suspension is prepared by suspending the platelet pellet in 2 ml of PBS (without $Ca^{2+}$ or $Mg^{2+}$) for each rat used. An aliquot of 200 ul of the rat platelet suspension thus obtained is incubated with 24 ul of test compound or solvent (DMSO; final concentration of 0.1%) for 5 min at 30°. The total assay volume is 244 ul. The reaction is initiated by the addition of 20 ul of a calcium/($^{14}$C)-AA solution (final concentration of 1.42 mM and 4 uM, respectively). After 3 min at 30°, the reaction is quenched by the addition of 15 ul of citric acid (1 M) and NDGA (5 mM).

Unlabeled 15-HETE and ($^3$H)-12-HETE are added to the citric acid quenched samples as internal standards. After chromatography of the extracted products on silica gel, ($^{14}$C)-12-HETE is located by the UV absorbence of the added 15-HETE (with which it co-chromatographs) and is quantitated by scintillation spectroscopy.

Table I shows the concentration required for inhibition of the 12-lipoxygenase (12-LOX/I$_{50}$ um) for representative compounds according to the present invention.

Protocol for Detecting Inhibitors of the Lipoxygenase Pathway (5-LOX Rat PMN)

A suspension of rat neutrophils in buffer is incubated for 3 min at 30° C. with [$^{14}$C]-arachidonic acid (AA) and calcium ionophore A23187. Citric acid (2M) is used to quench the reaction. Following the addition of a trace amount of ($^3$H)-5-HETE together with an excess of unlabeled 5-HETE to each tube, the mixture is extracted with chloroform/methanol. The organic layer is washed with dilute acid and an aliquot is transferred to glass tubes and dried. The residue is dissolved in a small volume of chloroform and an aliquot is spotted on silica gel TLC sheets which are developed with an ethyl acetate/isooctane/water/acetic acid solvent system. The 5-HETE spots are visualized with iodine, cut out and placed in scintillation vials for counting. After adjusting the extraction efficiency, the amount (pmole) of [$^{14}$C]-5-HETE in each of the tubes is quantitated. The net pmoles of 5-HETE are obtained by subtracting the pmoles of 5-HETE in the tubes containing buffer alone (blank) from the pmoles of 5-HETE in the tubes containing buffer and cells (control). The ability of the test compounds to modulate the activity of this enzyme is determined by a decrease or increase in the net amount of 5-HETE produced.

Table I shows the concentration required for inhibition of the 5-lipoxygenase (5-LOX/I$_{50}$ um) for representative compounds according to the present invention.

Protocol for the Biosynthesis of 5-HETE
(5(S)-Hydroxyeicosatetraenoic Acid) by Human Polymorphonuclear Leukocytes In Vitro (5-LOX Human PMN)

A. Isolation of Human Neutrophils

Freshly drawn venous blood from healthy human volunteers is mixed with 2 mM ethylenediamine tetraacetic acid and is sedimented at 1×g over 6% destran-saline. The leukocyte layer is aspirated, and the cells are concentrated by centrifugation and are layered over stacked Percoll ® solutions having densities of 1.072, 1.082 and 1.100, respectively. PMNs are isolated at the interface between the two densest layers after centrifugation at 400×g. Contaminating red blood cells are lysed by a short treatment of 0.16 M ammonium chloride.

B. The Assay

A suspension of human neutrophils in buffer is incubated for 3 min at 30° C. with ($^{14}$C)-arachidonic acid (AA) and calcium ionophore A23187. Citric Acid (2M) /NDGA* (10 mM) is used to quench the reaction. Following the addition of a trace amount of ($^3$H)-5-HETE together with an excess of unlabeled 5-HETE to each tube, the mixture is extracted with chloroform/methanol. The organic layer is washed with dilute hydrochloric acid and the total volume is transferred to glass tubes and dried in vacuo. The residue is dissolved in a small volume of chloroform and is spotted on silica gel TLC sheets which are developed with an ethyl acetate/isooctane/water/acetic acid solvent system

* NDGA - nordihydroguaiaretic acid (11/5/10/1 v/v). The 5-HETE spots are visualized under UV light, cut out and placed in scintillation vials for quantitation of radioactivity. After adjusting for the extraction efficiency, the amount (pmole) of ($^{14}$C)-5-HETE in each of the tubes is calculated. The net pmoles of 5-HETE are obtained by subtracting the pmole of 5-HETE in the tubes containing buffer alone (blank) from the pmoles of 5-HETE in the tubes containing buffer and cells (control). The ability of the test compound to modulate the activity of this enzyme is determined by a decrease or increase in the net amount of 5-HETE produced. This assay is a modification of that described by Bach and Brashler for rat peritoneal cells: Bach, M., Brashler, J.: Ionophore A23187-Induced Production of SRS-A by Rat Peritoneal Cells In Vitro: Evidence for Production by Mononuclear Cells, J. Immunol., 120, 998–1005 (1978).

Table I shows the concentration required for inhibition of the 5-lipoxygenase (5-LOX/I$_{50}$ um) for representative compounds according to the present invention.

Another assay has been developed to test the ability of the invented compounds on the activity of cyclooxygenase, which is one of the enzymes metabolizing arachidonic acids. By-products of arachidonic acid metabolism include thromboxanes, a type of which is designated as TXB$_2$, and protoglandins, a class of which is known as PGF$_2$. As indicated, supra, these by-products promote inflammatory response to a host of offending stimuli. The following protocol describes a procedure for testing the inhibitory effect on the production of TXB$_2$ and PGF$_2$.

Protocol for Detecting the Production of TXB$_2$ and PGF$_2$ (Rat PMN Cyclooxygenase)

A suspension of glycogen elicited rat peritoneal leukocyte-homogenate in buffer is incubated with ($^{14}$C)-arachidonic acid (AA), epinephrine and glutathione for 30 min at 37°. The reaction is quenched with 2M citric acid and a trace amount of ($^3$H)-TXB$_2$ and an excess of unlabeled TXB$_2$ and PGF$_2$ are added to each tube. After extraction of the mixture with chloroform/methanol, the organic layer is washed with dilute hydrochloric acid followed by evaporation in vacuo. The residue is dissolved in a small volume of chloroform and is spotted on silica gel TLC sheets which are developed in an ethyl acetate/isooctane/water/acetic acid solvent system. Spots containing TXB$_2$ and PGF$_2$ are visualized with iodine. Strips containing the spots are cut out, placed in scintillation vials and the radioactive content is quantitated in a liquid scintillation spectrometer.

After adjusting for the extraction efficiency, the amount (pmole) of ($^{14}$C)-TXB$_2$ and PGF$_2$ in each of the tubes is calculated. The net pmole of product is obtained by subtracting the pmole of TXB$_2$ and PGF$_2$ in the tubes containing buffer alone (blank) from the pmole of TXB$_2$ and PGF$_2$ in the tubes containing buffer and cellular homogenate (control). The ability of the test compounds to modulate the activity of this enzyme is determined by a decrease or increase in the net amount of TXB$_2$ and PGF$_2$ produced.

Table I shows the concentration required for inhibition of the cyclogenase (cyclox/I$_{50}$ um) for representative compounds of the present invention.

TABLE I

| Compound | $I_{50}$, uM | | | |
|---|---|---|---|---|
| | Rat PMN | 5-LOX Human PMN | 12-LOX Rat Platelet | CYCLOX Rat PMN |
| 3-amino-1-(4-benzyloxyphenyl)-2-pyrazoline | 0.7 | 6 | 2.8 | 40 |
| 3-amino-1-(3-benzyloxyphenyl)-2-pyrazoline | 0.5 | 0.1 | 36% (30 uM) | 30 |
| 3-propylamino-1-(4-benzyloxyphenyl)-2-pyrazoline | 50% (10 uM) | | | |
| 3-amino-1-(4-methoxyphenyl)-2-pyrazoline (compound of G.B. 2,093,832A) | 21% (10 uM) | | | |

A comparison of the biological results of the present invention with the closest compound encompassed within the claims of U.K. patent application No. GB 2 093 832A, namely, 3-amino-1-(4-methoxyphenyl)-2-pyrazoline, shows that the compounds of the present invention have superior activity in the 5-LOX RAT PMN assay and are therefore more effective and efficient as an anti-inflammatory, anti-hypersensitive and anti-allergic agent.

What is claimed is:

1. A compound of the formula:

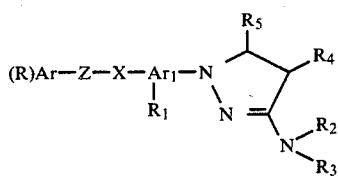

wherein

Ar and $Ar_1$ are each independently phenyl, naphthyl, quinoline, pyridine or benzothiophene;

Z is methylene or ethylene;

X is O or S;

R and $R_1$ are independently hydrogen, hydroxy, alkyl, carboxy, lower alkyl, carboxy, lower alkoxy, lower alkanoyloxy, halo, cyano, carboloweralkoxy, carboxyloweralkyl, phenoxy or benzyloxy;

$R_2$, $R_3$, $R_4$ and $R_5$ are independently hydrogen, lower alkyl, phenylloweralkyl, lower alkenyl, lower alkynyl, phenyl or carboxyloweralkyl;

or a pharmaceutically acceptable salt thereof.

2. The compound according to claim 1 wherein $R_2$ and $R_3$ are each independently H or lower alkyl.

3. The compound according to claim 1 wherein X is oxygen.

4. The compound according to claim 1 wherein R, $R_1$, $R_4$ and $R_5$ are hydrogen.

5. A compound of the formula:

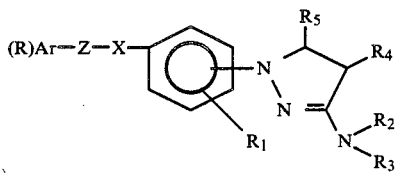

wherein

Ar is a phenyl, napthyl, quinoline, pyridine or benzothiophene;

Z is methylene or ethylene;

X is O or S;

R and $R_1$ are independently hydrogen, hydroxy, lower alkyl, carboxy, lower alkoxy, lower alkanoyloxy, halo, cyano, carboloweralkoxy, carboxyloweralkyl, phenoxy or benzyloxy;

$R_2$, $R_3$, $R_4$ and $R_5$ are independently hydrogen, lower alkyl, phenylloweralkyl, phenyl, loweralkenyl, loweralkynyl or carboxyloweralkyl;

or a pharmaceutically acceptable salt thereof.

6. The compound according to claim 5 wherein $R_2$ and $R_3$ are each independently H or lower alkyl.

7. The compound according to claim 5 wherein X is oxygen.

8. The compound according to claim 5 wherein R, $R_1$, $R_4$ and $R_5$ are hydrogen.

9. A compound of the formula:

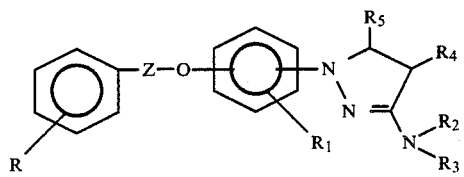

wherein

Z is methylene or ethylene,

R and $R_1$ are independently hydrogen, hydroxy, loweralkyl, carboxy, lower alkoxy, lower alkanoyloxy, halo, cyano, carboloweralkoxy, carboxyloweralkyl, phenoxy or benzyloxy;

$R_2$, $R_3$, $R_4$ and $R_5$ are independently hydrogen, loweralkyl, phenylloweralkyl, lower alkenyl, lower alkynyl, phenyl or carboxyloweralkyl;

or pharmaceutically acceptable salt thereof.

10. The compound according to claim 9 wherein $R_2$ and $R_3$ are each independently H or lower alkyl.

11. The compound according to claim 9 wherein R, $R_1$, $R_4$ and $R_5$ are hydrogen.

12. A compound of the formula:

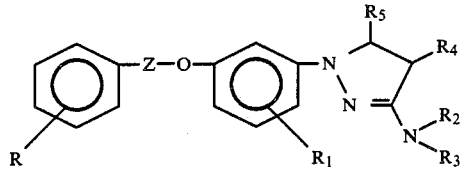

or

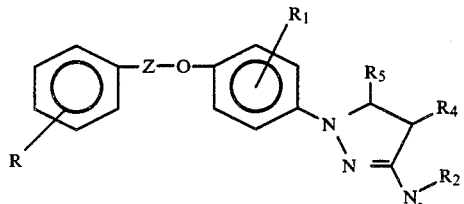

wherein

Z is methylene or ethylene,

R and $R_1$ are independently hydrogen, hydroxy, lower alkyl, carboxy, lower alkoxy, lower alkanoyloxy, halo, cyano, carboloweralkoxy, carboxyloweralkyl, phenoxy or benzyloxy;

$R_2$, $R_3$, $R_4$ and $R_5$ are independently hydrogen, lower alkyl, phenyloweralkyl, phenyl, lower alkenyl, lower alkynyl or carboxyloweralkyl;

or a pharmaceutically acceptable salt thereof.

13. The compound according to claim 12 wherein R, $R_1$, $R_4$ and $R_5$ are H.

14. The compound according to claim 12 wherein $R_2$ and $R_3$ are each independently H or lower alkyl.

15. The compound according to claim 1 which is 3-amino-1-(3-benzyloxybenzyl)-2-pyrazoline.

16. The compound according to claim 1 which is 3-amino-1-(4-benzyloxybenzyl)-2-pyrazoline.

17. The compound according to claim 1 which is 3-ethylamino-1-(4-benzyloxybenzyl)-2-pyrazoline.

18. The compound according to claim 1 which is 3-Amino-1-(3-(2-quinolinylmethoxy)phenyl)-2-pyrazoline.

19. The compound according to claim 1 which is 3-Benzylamino-1-(3-benzyloxyphenyl)-2-pyrazoline.

20. The compound according to claim 1 which is 3-(Butylamino)-1-(3-benzyloxyphenyl)-2-pyrazoline.

21. The compound according to claim 1 which is 3-(4-Carboxybutylamino)-1-(3-phenylethoxyphenyl)-2-pyrazoline.

22. The compound according to claim 1 which is 3-Amino-1-(5-benzyloxy-2-pyridyl)-2-pyrazoline.

23. The compound according to claim 1 which is 3-Amino-1-(7-benzyloxy-2-quinolinyl)-2-pyrazoline.

24. The compound according to claim 1 which is 3-Amino-1-(2-benzothiophenenylethoxyphenyl)-2-pyrazoline.

25. The compound according to claim 1 which is 3-Propylamino-1-(4-benzyloxyphenyl)-2-pyrazoline.

26. The compound according to claim 1 which is 3-Pentylamino-1-(3-benzyloxyphenyl)-2-pyrazoline.

27. A therapeutic composition for treating hypersensitivity disease, inflammatory conditions or allergic responses, comprising a therapeutically effective amount of a compound of claim 1 and a pharmaceutical carrier therefor.

28. A method of treating hypsensitivity disease, inflammatory conditions or allergic responses comprising the administration of a therapeutically effective amount of a compound according to claim 1.

* * * * *